United States Patent [19]

Guthrie et al.

[11] Patent Number: 5,241,262

[45] Date of Patent: Aug. 31, 1993

[54] CONTINUOUS-USE MOLTEN METAL INCLUSION SENSOR

[75] Inventors: Roderick I. L. Guthrie, Montreal, Canada; Hidemasa Nakajima, Kashima, Japan

[73] Assignees: R. Guthrie Research Associates Inc., Quebec, Canada; Sumito Metal Industries Inc., Igaragi, Japan

[21] Appl. No.: 768,713

[22] PCT Filed: Apr. 27, 1990

[86] PCT No.: PCT/CA90/00141

§ 371 Date: Oct. 28, 1991

§ 102(e) Date: Oct. 28, 1991

[87] PCT Pub. No.: WO90/13015

PCT Pub. Date: Nov. 1, 1990

[30] Foreign Application Priority Data

Apr. 27, 1989 [JP] Japan ................................ 1-108872

[51] Int. Cl.⁵ ........................ G01N 27/07; G01R 27/22
[52] U.S. Cl. ................................. 324/71.1; 324/71.4; 324/717; 324/724; 266/99; 164/4.1
[58] Field of Search ............... 324/71.1, 71.4, 691, 324/693, 713, 717, 724; 266/99; 164/4.1

[56] References Cited

U.S. PATENT DOCUMENTS

| | | |
|---|---|---|
| 3,259,841 | 7/1966 | Proctor et al. . |
| 3,395,343 | 7/1968 | Morgan et al. . |
| 3,963,984 | 6/1976 | Coulter . |
| 4,413,810 | 11/1983 | Tenberg et al. . |
| 4,468,009 | 8/1984 | Clauss et al. ............ 266/99 |
| 4,555,662 | 11/1985 | Doutre et al. . |
| 4,600,880 | 7/1986 | Doutre et al. . |
| 4,697,453 | 10/1987 | Murakawa et al. ......... 266/99 X |
| 4,763,065 | 8/1988 | Hachey . |

FOREIGN PATENT DOCUMENTS

| | | |
|---|---|---|
| 0165035 | 12/1985 | European Pat. Off. . |
| 0245010 | 11/1987 | European Pat. Off. . |
| 56-8527 | 1/1981 | Japan . |
| 56-104504 | 8/1981 | Japan . |
| 56-104505 | 8/1981 | Japan . |
| 56-107541 | 8/1981 | Japan . |

OTHER PUBLICATIONS

Kuyucak et al., On-line Inclusion Detection And Measurement In A Tranformer Steel, 2nd symp. on the effects and control of inclusion and residual in steels, Aug. 1986, pp. I44-I61.

Kuyucak et al, On The Measurement Of Inclusions In Copper-Based Melts, Canadian Metallurgical Quarterly, vol. 28, No. 1, pp. 41-48, Dec. 1989.

Ono, A., "Development of Direct Analysis Method for Molten Steel," pp. 51-57 (1989) Dec., Abstract only.

van der Plaats, G. et al., "Size Determination of Conductive Particles with a Coulter Count," *Particle Size Analysis 1981*, pp. 208-215, Dec.

Primary Examiner—Kennth A. Wieder
Assistant Examiner—Glenn W. Brown
Attorney, Agent, or Firm—Panitch, Schwarze, Jacobs & Nadel

[57] ABSTRACT

A molten metal inclusion sensor intended for "continuous" use in the testing of steel, i.e. a useful life of at least about 30 minutes, comprises a probe which is detachably connected to a water-cooled support member (35). The probe comprises a tube (30) of heat resistant material, preferably silica, having an inner electrode (31) mounted on its interior wall and an outer electrode (32) mounted on its exterior wall, the molten metal entering the tube interior through an orifice (33) upon its immersion in the molten metal, whereupon the flow of metal with entrained inclusions is monitored by measuring the voltage between the electrodes (31, 32). The electrodes (31, 32) are preferably of graphite and are shaped to fit closely against the walls of the part of the tube (30) that is immersed in the metal and are of a material that retains enough mechanical strength to support the tube (30) as the metal is pumped into and out of interior, the metal remaining hot enough for this pumping to occur. The orifice (33) is contoured to produce streamline flow and the Reynolds number of the flow preferably is kept below 2000.

7 Claims, 3 Drawing Sheets

CONTINUOUS-USE MOLTEN METAL INCLUSION SENSOR

TECHNICAL FIELD

This invention relates to an apparatus for detecting the content of inclusions in molten metal, such as precipitated secondary phase particles, drops of slag, and/or air bubbles, during refining thereof, all of which cause a discontinuity in the flow of current in the sensing zone and can therefore be sensed by measurement of this discontinuity. Hereinbelow, for convenience, all of these will be collectively referred to as "inclusions".

In general all such inclusions have a more or less deleterious effect upon the required technical properties of the metal, and it has become more and more essential to have accurate information as to their number and sizes, in order to confirm that the metal is sufficiently "clean" for its intended purpose, and also to show whether the processes employed are producing sufficiently "clean" metal.

INDUSTRIAL APPLICABILITY

The range of molten metals to which the present invention can be applied is board and includes molten metals subjected to refining in steel manufacture, aluminium refining, copper refining, titanium refining, magnesium refining, alloys of these metals, and the like. However, in the following description, molten steel in steel manufacture will be used primarily as an example.

BACKGROUND ART

One prior art invention which relates to the present invention is described in U.S. Pat. No. 4,555,662, issued November, 1985, this patent disclosing a quantitative measurement method for inclusions, the method now being generally referred to as Liquid Metal Cleanliness Analysis (LiMCA for short). The LiMCA method and apparatus were originally developed for detecting non-metallic inclusions during aluminium refining, but its application to iron and steel refining has also been investigated.

The LiMCA method is sometimes also referred to as the Electric Sensing Zone method (ESZ for short), the principle of the method being that when such an inclusion entrained in an electrically conductive fluid passes through an electrically-insulated orifice the electrical resistance of the fluid which is flowing through the orifice changes in proportion to the volume of the particle. The instantaneous change in the resistance is detected as a pulse in electrical potential between two electrodes on opposite sides of the orifice, and the number and size of the particles can be directly measured in the following manner.

First, if the particles are assumed to be spherical and of diameter d and the orifice is assumed to be cylindrical of diameter D, then the change R in the electrical resistance when a particle passes through the orifice is given by the following equation:

$$\Delta R = (4\rho d^3)/(\pi D^4) \quad (1)$$

Where $\rho$ is the electrical resistivity of the fluid.

In actual practice, Equation (1) must be corrected by a correction factor $F(d/D)$, which is given by the following equation:

$$F(d/D) = [1 - 0.8(d/D)^3]^{-1} \quad (2)$$

Thus, $\Delta R$ is actually expressed by the following equation:

$$\Delta R = ((4\rho d^3)/(\pi D^4)) \times [1 - 0.8(d/D)^3]^{-1} \quad (3)$$

If the electric current through the orifice is I, then the pulse V in the electric potential when a particle of diameter d passes through the orifice is given by the following equation:

$$\Delta V = i(\Delta R) \quad (4)$$

A previously-disclosed inclusion sensor probe which applies the above-described principles and intended for "continuous" use with molten metal (e.g. for periods as long as about 30–40 minutes) comprises an inner first electrode supported inside a quartz tube and connected to a water-cooled support. An orifice is provided in a portion of the quartz tube near to its lower end. The tube is mounted on the water-cooled support using a gasket to seal the joint between them. The necessary outer second electrode consists of a rod separate from the probe and extending close to the orifice.

When a measurement is to be performed the inside of the hollow electrode, which serves as a chamber to receive the molten metal, is evacuated and the molten metal is sucked inside through the orifice. At this time, the change in electric resistance between the inner and outer electrodes is measured and amplified by conventional means, and the sizes and number of inclusions are determined. When the tube is sufficiently full the negative pressure is replace by a positive pressure until the tube is empty and the cycle is repeated as many times as possible until the tube must be replaced.

The above-described sensor probe and others are used to perform "continuous" measurement by the LiMCA method in order to detect inclusions in molten aluminium and determine particle size distributions. Molten aluminium has a relatively low melting temperature of about 700° C., so there are a number of different materials available from which the tube (heat resistant glass and quartz) and the electrodes (steel wire) can be made. However, the working temperatures of molten metal baths of metals like iron and titanium are much higher than for aluminium (above 1550° C.), and at such temperatures there are considerable problems with lack of resistance of the probe and the electrodes to heat, so that it is difficult to employ these known sensors. There have been some applications of sensors of this type for measurement in the laboratory of inclusions of certain molten iron-silicon alloys having a temperature in the molten state of 1250° C.

In order to apply the LiMCA method to molten steel and the like, it is necessary to solve the following problems.

REQUIREMENT FOR FLOW OF MOLTEN METAL INTO AND OUT OF PROBE BODY

At the temperatures at which the sensor must operate it is difficult to find materials having the required properties of electrical insulation which are still sufficiently mechanically strong and are of sufficient low cost to be commercially acceptable. Normally to try to overcome this problem one would take all possible measures to cool the probe and its component part, but this is not possible with a sensor that is intended to operate continuously, since the first metal to enter would quickly freeze and could not subsequently be removed during the part of the cycle when the sensor is emptied for re-use. Therefore at least the part of the probe body that receives the molten metal must always be maintained at a temperature that is high enough that freezing, or even partial cooling for the metal to become too viscous, cannot occur, and it is this requirement that makes the provision of a satisfactory probe so difficult, and for which the present invention is a solution.

HEAT RESISTANCE OF A REFRACTORY PROBE BODY

When a probe is immersed in a molten metal with a high melting point, such as molten steel with a melting point of at least 1500° C., the temperature reached by the electrically insulating probe body may exceed the softening point of the material of which it is made. Therefore, when the molten metal is sucked inside the probe, and often before a single cycle can be completed, the probe body ends up buckling or deforming and subsequent measurement is impossible.

It is possible to make a probe body from a material such as boron nitride (BN) which has good resistance to high temperatures. However, such a probe body is extremely expensive (more than 10 times the cost of a quartz tube), and is therefore too costly to be employed in routine commercial operations.

MELTING DAMAGE OF THE INNER ELECTRODE AND POOR ELECTRICAL CONTACT DUE TO ADHESION OF SLAG, ETC.

In the prior art methods of which we are aware rod-shaped electrodes made of steel wire (or steel barstock), heat-resistant alloys, and the like were employed for the inner electrode. However, when the hot metal enters the probe even the first time, the rod-shaped metal electrode undergoes melting damage, and on the second and subsequent times the electrode may have become so short that it is difficult for the surface of the molten metal to reach its tip so that electrical contact is not achieved and measurement cannot be performed.

In order to cope with this problem, attempts have been made to use electrically conducting, heat-resistant materials such as graphite and zirconium boride ($ZrB_2$) for the inner electrode. However, during measurement a slag layer which is caused by the nonmetallic inclusions is formed on the surface of the electrode, and this leads to such poor electrical connection as to make measurement impossible.

MAINTAINING AIRTIGHTNESS BETWEEN PROBE HEAD AND PROBE BODY

The gasket or O-ring which is normally inserted between the probe head and the probe body to seal the joint is of course made of a heat-resistant material. In the case of a relatively low melting point metal such as aluminum, there is a correspondingly less problem with the sealing ability of the gasket. However, in the case of a high melting point metal such as molten steel, even if the probe head is water-cooled, the gasket or the O-ring are quickly deteriorated by heat conduction from the probe body and/or heat radiation from the surface of the molten metal, and as a result it quickly becomes impossible to maintain the airtightness of the inside of the probe during measurement.

In this case, not only does measurement become impossible due to the inability to such in or discharge molten metal, it also becomes difficult to accurately determine the amount of molten metal which was sucked in or discharged, and accurate determination of the concentration per unit volume of the particles being measured becomes impossible.

RESISTANCE TO MELTING OF THE HEAT-RESISTANT PROBE BODY

The outside of a heat-resistant probe body is corroded and subjected to melting damage by contact with the slag or flux which normally covers the surface of the molten metal and if holes are formed measurement becomes impossible. In order to prevent this it has been attempted to form the entirety of those portions of the probe body which are immersed from a slag-resistant material, such as boron nitride. However, these slag-resistant materials are expensive, so that with this proposal also the probe body becomes expensive and its cost makes it commercially uneconomical.

DISCLOSURE OF THE INVENTION

As a result of various investigations aimed at solving such problems, the present inventors have made the following invention.

In accordance with the present invention there is provided a molten metal inclusion sensor of the type which is immersed in a molten metal and detects inclusions in the molten metal by the electric sensing zone method, comprising a probe head and a probe supported by the probe head characterized in that the probe comprises a tube of electrically insulating material which constitutes a probe body, which tube is supported by the probe head and which is immersed in the molten metal and heated thereby, the tube having an orifice for the inflow and outflow of molten metal formed in the part of the tube that is immersed in the metal, an inner electrode having the form of an electrically conducting inner tube which is mounted on the inner wall of said tube, and an outer tube which is mounted on the outside of said, said inner and outer tubes providing physical support for at least the part of the probe body tube that is immersed in the metal.

In accordance with the present invention there is provided a molten metal inclusion sensor of the type which is immersed in a molten metal and detects inclusions in the molten metal by the electric sensing zone method, comprising a probe head and a probe supported by the probe head characterized in that the probe comprises a tube of electrically insulating material which constitutes a probe body, which tube is supported by the probe head and which is immersed in the molten metal and heated thereby, the tube having an orifice for the inflow and outflow of molten metal formed in the part of the tube that is immersed in the metal, an inner electrode having the form of an electrically conducting inner tube which is mounted on the inner wall of said tube, and an outer tube which is mounted on the outside wall of said tube, said inner and outer tubes providing physical support for at least the part of the probe body tube on which they are mounted and that in use is immersed in the metal.

Preferably, the said outer tube is of electrically conducting material and constitutes an outer electrode.

Preferably, the probe head that supports the probe body is water-cooled.

Preferably the material of the probe tube is silica and the material of the inner electrode or both the inner and outer electrodes is graphite.

MAINTAINING HEAT RESISTANCE OF THE PROBE BODY TUBE

Thus, the heat resistance of the probe body tube can be maintained or replaced by using as the inner electrode a tube of a material having high-temperature strength (i.e. one having a softening point temperature which is higher than the temperature of the molten metal) inside the probe body tube. The probe body is thereby supported against negative pressure during suction and positive pressure during evacuation, and even if the heat-resistant material of the probe body tube softens appreciably, the tube still will not buckle.

MELTING OF THE INNER ELECTRODE INSIDE THE PROBE, AND POOR ELECTRICAL CONTACT DUE TO ADHESION OF SLAG, ETC.

If the inner electrode is formed as a hollow, electrically conducting tube of heat-resistant material inserted inside the probe body and is made to function as the inner wall of the probe body metal-receiving enclosure, it not only functions as an inner electrode but upon melting the electrode material remains with the electrode and damage is prevented as much as is possible. Furthermore, the surface area of contact with the molten metal is increased, so that poor electrical contact is reduced. Also the structure of the probe body is simplified.

MAINTAINING AIRTIGHTNESS BETWEEN PROBE HEAD AND PROBE BODY

The following measures assist in counteracting against this problem.

(a) By inserting a heat insulating transverse member inside the probe body tube at the upper end of the inner electrode any sealing gasket and/or O-ring is insulated from heat radiation from the molten metal which flows into the probe body, and heat deterioration can thereby be reduced.

(b) Additionally or alternatively, if the probe head (and/or a probe holder which supports the probe body through a coupler between the probe head and the probe body) are water-cooled the effect on the gasket and/or O-ring of heat radiation from both inside and outside of the probe body can be minimized.

RESISTANCE TO MELTING DAMAGE OF HEAT-RESISTANT PROBE HEAD

If the outside of those portions of a heat-resistant probe body which may contact molten slag or flux as the probe is inserted into the melt are protected with a slag-resistant material melting damage of the probe body from the outside can be effectively prevented. With this method, two different modes are conceivable.

(A) A separate outer electrode is used and a nonconducting outer tube is mounted on the probe body, or (B) An outer tube made of an electrically conducting refractory is mounted on the probe body. In this case, the outer tube can be used as an outer electrode, and the heat resistance of the probe body is particularly improved.

DESCRIPTION OF THE DRAWINGS

The prior art ESZ method and apparatus will now be described in more detail, and a probe which is a preferred embodiment of the invention will now be described, by way of example, with reference to the accompanying drawings, wherein.

DESCRIPTION OF PRIOR ART METHOD AND APPARATUS

Figure 1:
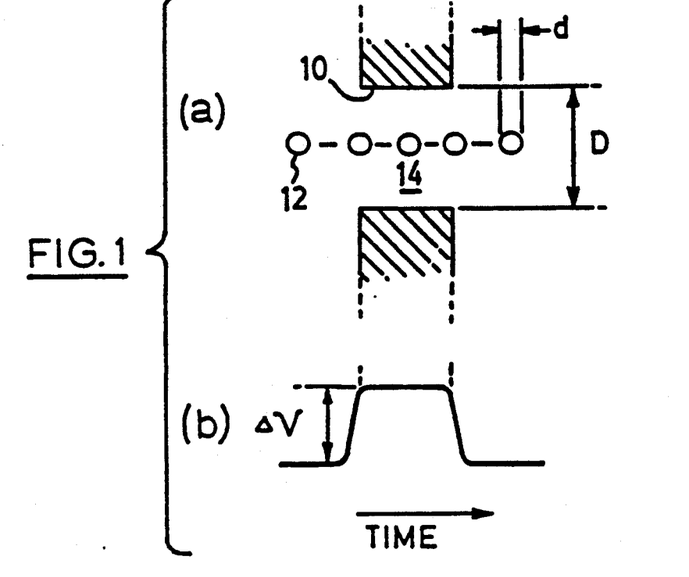
FIG. 1(a) and 1(b) are illustrations which explain the principles of inclusion detection by the ESZ method.
Figure 2:
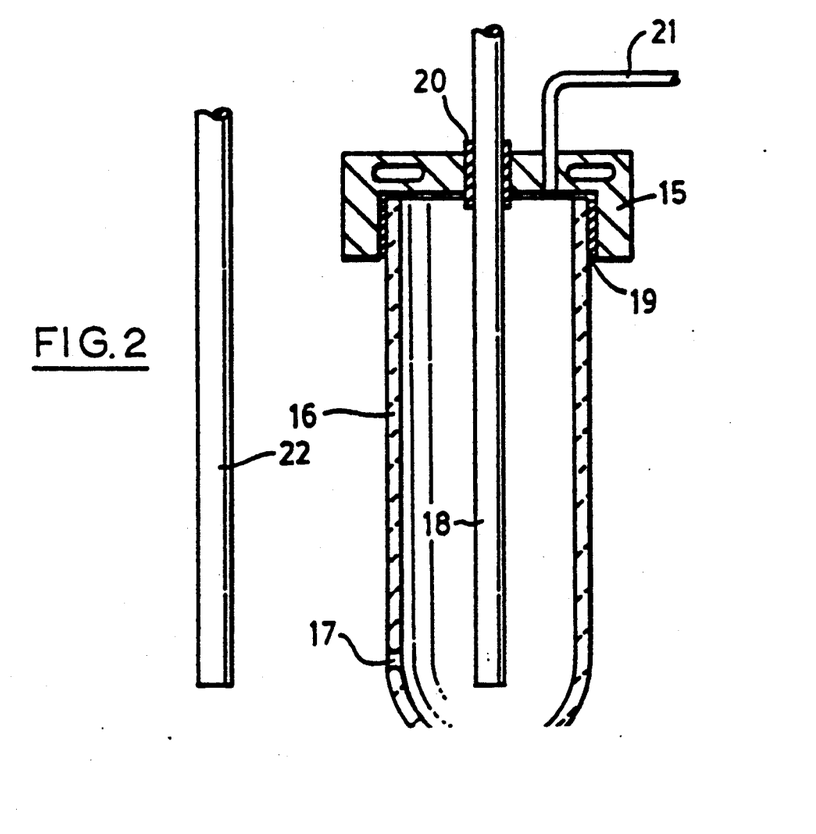
FIG. 2 is a longitudinal cross-sectional view of a continuous measurement prior art inclusion sensor probe which utilizes the ESZ method, and employs a separate outer electrode.

FIG. 1a illustrates an electrically-insulated orifice 10 of diameter D formed in a wall through which flows an electrically conductive fluid 14, namely molten metal. Non-conductive inclusion particles 12 of diameter d that are entrained in the fluid and flow through the orifice each give a respective resistance change and consequent electric potential pulse $\Delta V$ illustrated by FIG. 1b. FIG. 2 shows the probe of a prior art inclusion sensor which applies these principles and of the type having a separate outer electrode. In some cases, a level sensor is mounted inside the probe body.

A probe body 16 which is vertically supported by a water-cooled probe head 15 is constituted by an electrically insulating tube made of quartz, for example, an orifice 17 being formed near to its tip. A rod-like inner electrode 18 passes through the probe head 15 and is inserted into the interior of the electrically insulating tube, extending to the vicinity of the orifice 17. The probe body 16 is connected to the probe head 15 in an airtight manner by means of a gasket 19. The inner electrode 18 is also mounted on the probe head 15 in an airtight manner by means of an electrically insulating, heat-resistant gasket 20. The inside of the tube is connected to a suitable air supply and exhaust system through a pipe 21. When the probe body is immersed into molten metal air flows into and out of the tube through the orifice 17. An outer electrode 22 is disposed in a location confront the orifice 17.

The probe body 16 is immersed in the molten metal and then the exhaust system is operated to produce a vacuum inside the tube interior, causing flow of molten metal into the tube. The size and quantity of inclusions in the metal are then measured based on the change in the electrical resistance between the inner and outer electrodes. As described above this prior art sensor is used to perform "continuous" measurement by LiMCA in order to detect and measure inclusions in molten aluminium.

BEST MODES OF CARRYING OUT THE INVENTION

Figure 3:
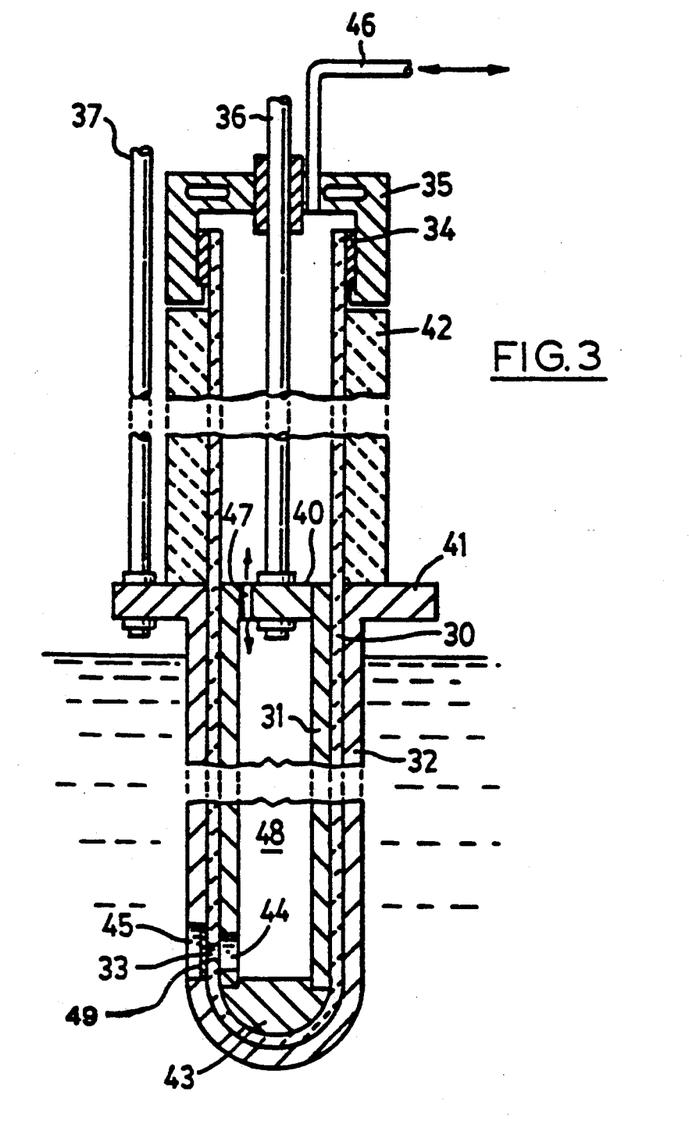
FIG. 3 is a longitudinal cross-sectional view of an inclusion sensor probe of the invention.

In the sensor of the invention shown in FIG. 3, an inner cylindrical electrode 31 and an outer cylindrical electrode 32 are electrically insulated from one another by an interposed, elongated tube 30 of electrically-insulating, heat-resistant material, in this embodiment a quartz tube, which constitutes the probe body. The lower portion of the tube 30 is provided with an orifice 33 in the same manner as in FIG. 2. When the probe is immersed in molten metal and a vacuum is applied to the pipe 46, the molten metal is sucked into the tube 30 through the orifice 33. The tube 30 is supported by a water-cooled probe head 35 at its top end, a pressure-sealing gasket 34 being interposed between them. The probe is moved into and out of the metal by any suitable handling mechanism (not shown) attached to the probe head 35. The inner and outer electrodes 31 and 32 are respectively connected to electrode rods 36 and 37. A cover member 40 for the upper end of the inner tube constitutes a heat-insulating shield member shielding the upper portion of the tube from heat from the molten metal in the lower portion.

The lower end of the inner electrode is provided with a shaped end portion 43 which fits snugly into the lower end of the tube, while the outer electrode is also shaped to fit snugly around the rounded outer end of the tube 30. The inner and outer electrodes are provided with respective apertures 44 and 45 surrounding the orifice 33 and through which the molten metal passes. The lower end of the tube which is inserted into the molten metal is therefore substantially entirely sandwiched, enclosed and supported between the two electrodes 31 and 32, and only the small portion adjacent the orifice is directly exposed to the molten metal. The shield member 40 is provided with a bore 47 through which the vacuum and pressure are applied to the interior of metal receiving chamber 48, and thus also ensures that metal cannot splash and reach to the portion of the tube 30 that is not protected by the internal electrode 31 and the cover 40.

The preferred material for the inner electrode 31 and the heat-insulating member 40 is graphite, which as well as being electrically conductive, retains enough mechanical strength at the molten metal temperature to be able to support the probe body against collapsing due to softening when molten metal is sucked in and forced out. In addition, the inner electrode provides a large surface area of contact with the molten metal within the probe body and ensures good electrical contact.

The heat-insulating shield member 40 prevents the centre of the probe head 35 from overheating by radiation from the metal, and as a result the degradation and wear of the gasket 34 are at least substantially reduced. Therefore, good airtightness can be maintained between the probe head 35 and the probe body 30 for the period for which the sensor is operative, and the suction and discharge of molten metal into and from the electrically insulating tube 30 is carried out smoothly. In addition, because good sealing is maintained the pressure inside the probe body 30 can be measured accurately and it is possible to accurately determine the amount of molten metal which is sucked in or discharged, so that accurate measurement of the concentration of particles per unit volume can be performed.

The electrically conducting, heat-resistant inner electrode 31 is therefore used for the purpose of increasing the heat resistant strength of the probe body, for preventing the adhesion of slag to the insides of the probe body, and for preventing melting damage to the inner electrode. In addition, the probe head 35 is water-cooled in order to measure and maintain the airtightness between the probe head and the probe body. The outer electrode 32 which is also made from an electrically conducting, heat-resistant material also has resistance to slag erosion so it also functions as a slag protection layer. At the same time, as it is co-extensive with the probe body 30, it helps increase the compactness of an inclusion sensor in accordance with the present invention.

The upper end of the tube 30 that is not immersed in the molten metal is provided with an enclosing cylinder 42 of slag-protecting material, and the prevention of splashes and the effect of heat radiation from the bath of this upper end is also improved by the outwardly extending flange 41 of the outer cylinder 32, this flange effectively providing a demarcation between the part of the sensor that is immersed and the part that always remains above the surface of the bath. The slag layer may vary widely in thickness over a range of as much as 1–15 cm and a typical length for the tube 30 is 30–40 cm with an internal diameter typically of about 4–5 cm. The thickness of each of the inner and outer electrodes is typically 4–10 mm, more usually about 6 mm.

The orifice (33) may be provided with a thin metal cover 49 of a material of lower melting point than the metal bath that is melted by the molten metal once the probe is in the bath, the cover preventing entry of slag into the aperture 33 as it passes through the slag layer upon being first inserted into the bath. A suitable material is aluminium of thickness in the range 0.1–1.0 mm.

The size of the orifice 33 that is required can vary relatively widely, depending upon the metal whose cleanliness is being investigated and the nature of the inclusions therein. A minimum value typically is 200 microns, but some steels are found to have inclusions measuring as much as 250 microns, so that orifices as large as 1.2 mm may be required. Some of the inclusions found in steel, such as alumina and aluminosilicates, are known to have a tendency to adhere to refractory materials and it is important to prevent this from happening, since they may accumulate at the orifice and at least partly bock it. One way of at least reducing this effect is to shape the orifice so that both the entrance and the exit are smoothly rounded, thereby avoiding turbulence and recirculation of the ingoing flow as much as possible; the choice of the material for the tube 30 will be affected by the ease of economically producing such a contoured aperture. For example, with a silica tube it is found possible to produce the orifice economically by first drilling a hole using a watch-makers diamond drill and then heating the edges of the hole with a micro-torch (oxy-acetylene) to partially fuse the silica and allow surface energy forces to shape it to the required contour. The initial size of the hole is chosen to achieve the desired final size of orifice. With a long narrow tube, as is used for the probe, the entry can be shaped conveniently in this manner, but shaping the exit is more difficult and to facilitate this the orifice may be formed in a disc-shaped insert which is then mounted in a same-size aperture in the wall of the tube.

Another consideration in avoiding turbulence and consequent potential for clogging is to keep the Reynolds number of the flow to less than about 2000, since beyond this value the flow tends to become turbulent even if the flow path is "streamlined" by the contouring of the orifice. The Reynolds number is given by the relation:

$$R = \frac{\rho U d}{\mu}$$

where
$\rho$ = density of the fluid
$U$ = mean flow velocity
$d$ = diameter of orifice, and
$\mu$ = viscosity of the fluid It will be seen that $\rho$ and $\mu$ are set by the process being employed and only $U$ and $d$ can be determined by the design of the probe and are intimately related to one another. The choice of d is somewhat restricted in dependence upon the size of the inclusions to be measured, while the value of U can be controlled by the pressure difference that is used to move the metal. If a large orifice is needed it may be necessary to use a relatively lower pressure differential to slow the flow to the required extent.

Materials-Electrodes

In order to establish good electrical contact between the molten metal and the electrodes, without which the LiMCA signals will be obscured in a background of electrical noise, it is important that as much wetting as possible be established along the current path between the two electrodes and the electric sensing zone is between. From the point of view of choosing suitable electrodes, clearly they must not react with the melt to form an electrically insulating oxide, or other non-conducting layer.

Graphite is a much preferred material because of its cost but may present problems if the metal contains appreciable dissolved oxygen (e.g. above about 10 ppm) since there is then a tendency to produce CO bubbles which can produce spurious signals, or even block the signal path completely. One helpful technique is to employ a brief heavy "conditioning" current prior to the application of the test current, as is employed in the LiMCA technique, which is believed to help "burn-out" local areas of oxides or gas films in the orifice that otherwise produce increased electrical resistance between the electrode and the melt. In the case of molten steel, particularly aluminium killed steel with consequent low oxygen levels, graphite is a good choice in that it is a reasonably good conductor of electricity and dissolves only slowly in steel. Further, in low carbon melts, graphite has a contact angle that is a little less than 90°, i.e. it is slightly wetting which is again helpful. The net effect of choosing graphite is an electrode which practically instantaneously establishes good contact. Further, as graphite does not melt at typical steel-making temperatures (1500°-1650° C.) it is able to provide the required mechanical support to the probe body. Silica melts at about 1740° C. but is certainly somewhat softened at steel bath operating temperatures, and therefore needs such support.

MATERIALS—PROBE BODY

A preferred electrical and thermal insulating material for the portion of the probe containing the orifice 33 is fused silica, despite its softening, because of its ready availability, lower cost and the relative ease of forming a contoured orifice. Moreover, silica is chemically attacked by iron and steel and it appears that the orifice is cleaned (reamed) by the flow of metal through it, so that good signals are obtained. The use of a high initial conditioning current is also useful, and it is found that maximising the time of contact between the silica and the steel also appears to improve performance, against indicating against too rapid a flow rate.

Other suitable materials are boron nitride (BN) which has been employed, and titania ($TiO_2$), but these are both much more expensive than silica to the extent that the sensor may be commercially uneconomical. Boron nitride has been reported as having a contact angle with steel at 1550° C. of less than 50°, while titania has a contact angle with iron of 84°. Orifices are readily made in boron nitride but contouring of the edges is more difficult; melts with high oxygen content (e.g. greater than 1,000 ppm) should also be avoided since otherwise the boron nitride is quickly corroded.

The invention will now be explained in greater detail by means of the following examples.

EXAMPLES

In a first example the concentration of inclusions in molten metal steel was measured using an inclusion sensor of the invention having the structure shown in FIG. 3, the sensor having an aluminium probe head 35, a steel electrode rods 36 and 37, a graphite inner electrode 31, a graphite outer electrode 32, an electrically insulating quartz tube 30, and a heat-resistant rubber gasket 34.

When measurement was performed molten metal was at 1550° C. and a slag layer having a thickness of 10 mm was present atop the molten steel. Table 1 shows the composition of the molten steel, and Table 2 shows the composition of the molten slag.

TABLE 1

| MOLTEN STEEL COMPOSITION (WT %) | | | | | | |
|---|---|---|---|---|---|---|
| C | Si | Mn | P | S | sol. Al | Total $O_2$ |
| 0.05 | 0.12 | 0.60 | 0.018 | 0.006 | 0.045 | 0.0085 |

TABLE 2

| MOLTEN SLAG COMPOSITION (WT %) | | | | | |
|---|---|---|---|---|---|
| CaO | $SiO_2$ | $Al_2O_3$ | MgO | MnO | FeO |
| 32.4 | 24.7 | 18.7 | 10.1 | 8.8 | 5.3 |

It was found that this probe of the invention could perform continuous measurement with no problems encountered while immersed in molten steel for over 30 minutes.

COMPARATIVE EXAMPLE 1

In this example, a prior art type of inclusion sensor as illustrated by FIG. 2, having a probe body 16 made from a quartz tube, was used to measure the concentration of inclusions in molten steel in the same manner and with the same conditions as in Example 1. The probe body 16 was immersed in the molten steel and after approximately 3 minutes the pressure within the probe was reduced to 16.5 kPa, and the suction of the molten steel began. However, 15 seconds after the start of suction the probe body deformed and collapsed, due to the molten steel temperature which exceeded its softening point, and due to the negative pressure within the probe, and measurement became impossible. The probe head 15 was water-cooled, and the gasket 19 was still sound after the test.

COMPARATIVE EXAMPLE 2

Figure 4:
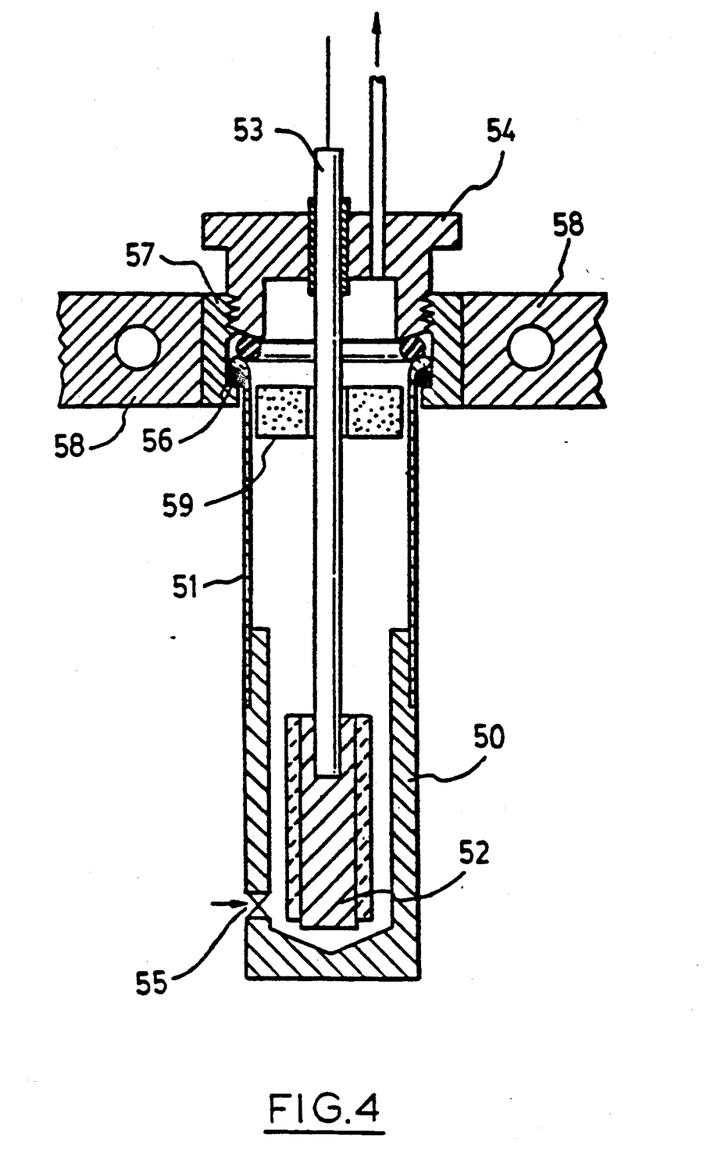
FIG. 4 is a similar view of FIG. 2 of another prior art sensor probe.

In this example, the measurement of inclusions in molten steel was performed in the same manner as in Example 1, using the inclusion sensor shown in FIG. 4 and under the same conditions. This employed a composite probe body the lower part 50 which was immersed in the steel being made of boron nitride (BN) with the upper part 51 that connected the lower part 50 to a coupler 57 made of silica. The inner electrode 52 was of graphite surrounded by a cylinder of mullite. The separate outer electrode is not shown, but the inner electrode 52 was connected to an electrode rod 53. The composite probe body 50, 51 was supported by a probe head 54 through a coupler 57 which is equipped with an O-ring 56, the coupler being connected to and supported by a water-cooled probe holder 58. Reference 59 indicates a radiation shield member made of a heat-insulating material, such as a heat-resistant inorganic fiber, and which protects the O-ring 56 from heat from the molten steel. Reference numeral 55 indicates the sensing orifice. The bath which was measured comprised the molten steel and the molten slag as described in Examples 1 and 2. As in example 1, approximately 3 minutes after immersion of the probe body the pressure within the probe body was reduced to 16.5 kPa to begin the suction. When the level of the molten steel within the probe body reached the tip of the inner electrode the detection of LiMCA signals commenced. Next, after the level of molten steel within the probe body reached a prescribed level, the suction was stopped and, the inside of the probe was then pressurized with argon gas, so that the molten steel was discharged. After the discharge of had been nearly completed, molten steel was again sucked into the probe body, and detection of signals due to inclusions was attempted a second time. However, even after the level of steel within the probe reached the inner electrode 52, the current through the signal detecting circuit was extremely unstable, and the oscillation of the base line (noise) on an oscilloscope far exceeded the peak height of the signals due to inclusions, and thus the detection and measurement of signals was impossible. The reason for this was that when the molten steel was discharged, a slag layer and an inclusion layer adhered to the entire surface of the small-diameter inner electrode, and the conductiveity of the electrode surface was greatly reduced.

COMPARATIVE EXAMPLE 3

In this example, Example 1 was repeated except that the probe which was employed was not equipped with a water-cooled probe head or a radiation shield. The molten bath which was measured comprised the molten steel and slag described in Tables 1 and 2 at 1550° C. The probe body was immersed in the molten steel for approximately 3 minutes, after which the pressure inside the probe was reduced to 16.5 kPa and the suction and detection and measurement of LIMCA signals began. Three minutes after the start of measurement it became difficult to suck or discharge the molten steel, and the detection and measurement of signals became impossible. The reason for this was that the O-ring which was made of heat-resistant rubber had burned due to radiation and conduction of heat from the molten steel, and the airtightness of the inside of the probe could not be maintained.

COMPARATIVE EXAMPLE 4

In this example Example 1 was repeated, but the probe body which was employed was not equipped with an outer tube and an outer electrode was employed. As with example 3, the bath comprised the molten steel and slag described in Tables 1 and 2 at 1550° C. Approximately three minutes after the probe body was immersed in the molten steel the inside of the probe was reduced to a pressure of 16.5 kPa and the suction and detection and measurement of LiMCA signals was begun. However, give minutes after the start of measurement the portion of the quartz tube constituting the probe body which contacted the molten slag suffered melting damage and holes were formed therein, so that subsequent measurement was impossible.

By way of summarizing the above results, the usable life of the probes in molten steel and their unit costs are compared in Table 3. The present invention is not particularly inexpensive from the standpoint of manufacturing costs, but it can be seen that is is overwhelmingly superior in its useful life.

TABLE 3

| Probe Type | Length of Normal Operation from Start of Suction of Molten Steel (minutes) | Cost per Probe * (Index) |
|---|---|---|
| Present Invention | At least 30 minutes | 100 |
| Comparative Example 1 | 15 seconds | 75 |
| Comparative Example 2 | At most 2 minutes (Only one measurement possible) | 600 |
| Comparative Example 3 | 3 minutes | 95 |
| Comparative Example 4 | 5 minutes | 95 |

* Note:
Does not include probe holder or probe head.

It will be seen that, as described above, an inclusion sensor in accordance with the present invention can perform continuous measurement of inclusions in a molten metal such as molten steel which has a high melting point, and as it can perform continuous measurement for over 30 minutes, it can be said to be a superior inclusion sensor for practical use.

| Index of Reference Signs | |
|---|---|
| 10 | Prior Art - insulated orifice |
| 12 | Prior Art - non-conducting particles |
| 14 | Prior Art - electrically-conducting fluid |
| 15 | Prior Art - water-cooled probe head |
| 16 | Prior Art - probe body |
| 17 | Prior Art - orifice |
| 18 | Prior Art - inner electrode |
| 19 | Prior Art - tube/head gasket |
| 20 | Prior Art - head/electrode gasket |
| 21 | Prior Art - pressure/exhaust pipe |
| 22 | Prior Art - separate outer electrode |
| 30 | quartz tube |
| 31 | inner electrode |
| 32 | outer electrode |
| 33 | orifice |
| 34 | tube/head gasket |
| 35 | water-cooled probe head |
| 36 | inner electrode rod |
| 37 | outer electrode rod |
| 38 | head electrode gasket |
| 40 | heat insulating shield member |
| 41 | heat shielding flange |
| 42 | slag protecting envelope |
| 43 | inner electrode end |
| 44 | inner electrode aperture |
| 45 | outer electrode aperture |
| 46 | pipe to pressure/vacuum source |
| 47 | bore for pressure/vacuum passage |
| 48 | metal receiving chamber |
| 49 | orifice cover |
| 50 | Prior Art - probe body lower part |
| 51 | Prior Art - probe body upper part |
| 52 | Prior Art - inner electrode |
| 53 | Prior Art - inner electrode rod |
| 54 | Prior Art - probe head |
| 55 | Prior Art - orifice |
| 56 | Prior Art - O-ring |
| 57 | Prior Art - coupler |
| 58 | Prior Art - water-cooled probe holder |
| 59 | Prior Art - radiation shield |

We claim:

1. A molten metal inclusion sensor of the type which is immersed in molten metal and detects inclusions in the molten metal by the electric sensing zone method, the sensor comprising:

a probe head and a probe body supported by the probe head, the probe body having an upper end and a lower end so that the probe body is movable for immersion of said lower end in the molten metal by which the probe body is heated;

the probe body comprising:

an elongated insulating tue of electrically insulating material that engages the probe head for its support thereby and resultant support of the probe body by the probe head, the insulating tube having an upper end and a lower end corresponding to the upper end and lower end of the probe body, respectively;

an inner electrode having the form of an electrically conducting inner tube mounted on an inner wall of the insulating tube so as to extend from the lower end of the insulating tube to a position intermediate the length of the insulating tube;

the inner tube electrode comprising a metal-receiving chamber having at an upper end a transversely extending, heat-insulating cover member inhibiting movement of molten metal to the upper end of the insulating tue and shielding the upper end of the insulating tube from the heat of metal in the metal-receiving chamber;

an outer electrode having the form of an electrically conducting outer tue mounted on an outer wall of the insulating tube so as to extend from the lower end of the insulating tube to the position intermediate the length of the insulating tube and above the molten metal when the probe body is inserted in the molten metal;

the outer tube electrode having at an upper end a circumferential shield shielding the upper end of the insulating tube from heat radiated from the molten metal;

said inner and outer tube electrodes providing physical support for at least the part of the insulating tube on which they are mounted being immersed in the metal during use; and the insulating tube and the inner and outer electrodes including registering orifices for the inflow and outflow of metal between the metal-receiving chamber and the molten metal.

2. A sensor as claimed in claim 1, wherein the probe head (35) that supports the probe body is water-cooled.

3. A sensor as claimed in claim 1, wherein the insulating tube (30) is comprised of silica and the inner and outer electrodes (31, 32) are comprised of graphite.

4. A sensor as claimed in claim 1, further comprising a cylinder (42) of slag protecting material disposed around the upper part of the probe body above the outer tube (32) to shield the probe body from slag on the surface of the molten metal when the probe body is inserted into the molten metal.

5. A sensor as claimed in claim 1, wherein the probe is provided with an external cover member (49) covering the orifice (33) comprised of a material having a lower melting point than the temperature molten metal, the cover member (49) permitting the probe to be passed through a layer of slag on the surface of the molten metal without entry of slag into the metal-receiving chamber (48).

6. A sensor as claimed in claim 1, wherein the orifice (33) has a contoured profile and entrance and exit openings smoothly rounded to reduce turbulence of flow therethrough.

7. A sensor as claimed in claim 1, wherein the rate of flow of the molten metal into the probe is such that the Reynolds number is less than 2,000.

* * * * *